United States Patent [19]

Drabek et al.

[11] 4,153,723
[45] May 8, 1979

[54] ANTHELMINTIC AGENTS

[75] Inventors: Jozef Drabek, Oberwil; Alfred Meyer, Basel, both of Switzerland

[73] Assignee: Ciba-Geigy Corporation, Ardsley, N.Y.

[21] Appl. No.: 867,650

[22] Filed: Jan. 6, 1978

[30] Foreign Application Priority Data

Jan. 10, 1977 [CH] Switzerland ............................ 267/77
Dec. 7, 1977 [CH] Switzerland ........................... 15002/77

[51] Int. Cl.² ....................... A01N 9/20; C07C 121/78
[52] U.S. Cl. .................................. 424/304; 260/465 E
[58] Field of Search ...................... 260/465 E; 424/304

[56] References Cited

U.S. PATENT DOCUMENTS

| | | | |
|---|---|---|---|
| 3,551,573 | 12/1970 | Baker et al. | 424/304 |
| 3,702,861 | 11/1972 | Howe | 260/465 E |
| 3,982,015 | 9/1976 | Drabek | 424/304 |
| 4,000,314 | 12/1976 | Drabek | 424/304 |

Primary Examiner—Dolph H. Torrence
Attorney, Agent, or Firm—Harry Falber

[57] ABSTRACT

This invention concerns novel anilinomethylenemalononitrile derivatives corresponding to the formula I

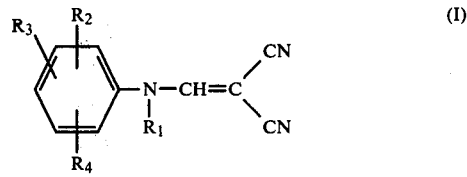

wherein
$R_1$ represents halogenalkyl containing 1 to 6 carbon atoms in the alkyl moiety, $C_3$–$C_4$ alkenyl, $C_3$–$C_5$ alkynyl or a benzyl radical which is unsubstituted or substituted by 1 to 2 halogen atoms, 1 to 2 $C_1$–$C_2$ alkyl radicals, or by a cyano or a trifluoromethyl group,
$R_2$ represents hydrogen, $C_1$–$C_4$ alkyl, halogen, the trifluoromethyl group, the nitro group or the cyano group,
$R_3$ represents hydrogen, halogen, the trifluoromethyl group or the nitro group, and
$R_4$ represents hydrogen or halogen, with the proviso that, if $R_1$ represents the $C_3$ alkynyl radical or the unsubstituted benzyl group, $R_2$ and $R_3$ may not be trifluoromethyl, compositions containing the novel compounds and the use of the novel compounds for combating helminths in domestic animals and productive livestock.

5 Claims, No Drawings

ANTHELMINTIC AGENTS

The present invention relates to novel anilinomethylene-malononitrile derivatives having anthelmintic action, to a process for producing these compounds, to compositions which contain them as active component and to a method of combating helminths, especially of *Fasciola hepatica*, in domestic animals and productive livestock, which comprises the use thereof.

The compounds of the present invention have the general formula I

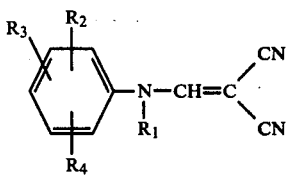

(I)

wherein
  $R_1$ represents halogenalkyl containing 1 to 6 carbon atoms in the alkyl moiety, $C_3$-$C_4$ alkenyl, $C_3$-$C_5$ alkynyl or a benzyl radical which is unsubstituted or substituted by 1 to 2 halogen atoms, 1 to 2 $C_1$-$C_2$ alkyl radicals, or by a cyano or a trifluoromethyl group,
  $R_2$ represents hydrogen, $C_1$-$C_4$ alkyl, halogen, the trifluoromethyl group, the nitro group or the cyano group,
  $R_3$ represents hydrogen, halogen, the trifluoromethyl group or the nitro group, and
  $R_4$ represents hydrogen or halogen,
with the proviso that, if $R_1$ represents the $C_3$ alkynyl radical or the unsubstituted benzyl group, $R_2$ and $R_3$ may not be trifluoromethyl.

Active compounds distinguished by a particularly outstanding anthelmintic action are those which fall under the following restricted formula Ia

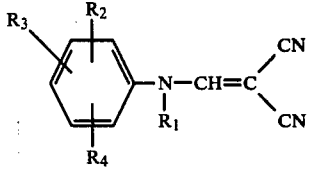

(Ia)

wherein
  $R_1$ represents halogenalkyl containing 1 to 6 carbon atoms in the alkyl moiety, $C_3$-$C_4$ alkenyl, $C_3$-$C_5$ alkynyl or a benzyl radical which is unsubstituted or substituted by 1 to 2 halogen atoms, 1 to 2 $C_1$-$C_2$ alkyl radicals, or by a cyano or trifluoromethyl group,
  $R_2$ and $R_3$, each independently of the other, represent hydrogen, halogen, methyl, the trifluoromethyl or nitro group, and
  $R_4$ represents hydrogen or halogen,
with the proviso that, if $R_1$ represents the $C_3$ alkynyl radical or the unsubstituted benzyl radical, $R_2$ and $R_3$ may not be trifluoromethyl.

Within the group of anthelmintic active compounds of the formula I referred to above, compounds which may be regarded as especially active against trematoda are those of the following restricted formula Ib

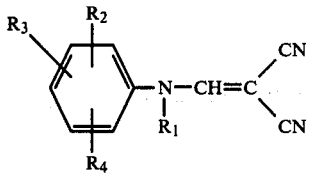

(Ib)

wherein
  $R_1$ represents halogenalkyl containing 1 to 6 carbon atoms in the alkyl moiety, $C_3$-$C_4$ alkenyl, $C_3$-$C_5$ alkynyl or a benzyl radical which is unsubstituted or substituted by 1 to 2 halogen atoms, 1 to 2 $C_1$-$C_2$ alkyl radicals or by a cyano or trifluoromethyl group,
  $R_2$ and $R_3$, each independently of the other, represent chlorine, methyl, the trifluoromethyl group or the nitro group, and
  $R_4$ represents hydrogen or chlorine,
with the proviso that, if $R_1$ represents the $C_3$ alkynyl radical or the unsubstituted benzyl radical, $R_2$ and $R_3$ may not be trifluoromethyl.

The term "halogen" is to be understood as meaning fluorine, chlorine, bromine and iodine.

The alkyl, alkenyl and alkynyl radicals can be straight-chain or branched. Examples of alkyl radicals are: methyl, ethyl, n-propyl, isopropyl, n-butyl, isobutyl, sec-butyl, tert-butyl, n-amyl, isoamyl as well as the isomers of the hexyl radical. Examples of alkenyl radicals are: propenyl, allyl, methylvinyl and pentadienyl. Alkynyl radicals are for example: propynes, such as propargyl as well as butynes and pentynes. The halogenalkyl radicals contain 1 to 4 halogen atoms, namely fluorine, chlorine, bromine and iodine atoms.

The compounds of the formula I can be obtained by methods which are known per se, for example by the process known from U.S. Pat. No. 3,551,573 by introducing the radical $R_1$ in place of the hydrogen atom located at the nitrogen atom of the aniline radical according to the reaction scheme:

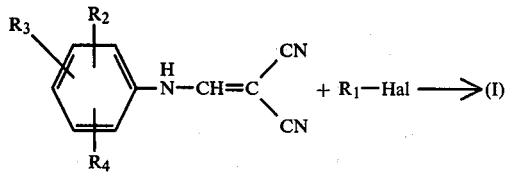

(II)     (III)

wherein $R_1$ to $R_4$ are as defined in formula I and Hal represents halogen. The reaction is carried out preferably in solvents and/or diluents which are inert to the reactants, for example ketones, nitriles, ethers, formamidines and dimethyl sulphoxide and hexamethyltriamidophosphate. Suitable acid acceptors are sodium or potassium hydroxide, alkaline alcoholates, pyridine or tertiary amines. Furthermore, it is also possible to use instead the alkali metal salts of the starting materials. In addition, catalysts, such as sodium iodide or potassium iodide, can be used to increase the reaction rate.

The reaction temperatures suitable for carrying out the individual reactions depend on the respective reactants and are between 0° and 100° C.

The starting materials are in part known and described in U.S. Pat. Nos. 3,551,573, 3,629,448, 3,691,222 and 3,726,662. If they are new, they can in principle be prepared in a manner known per se in the following manner:

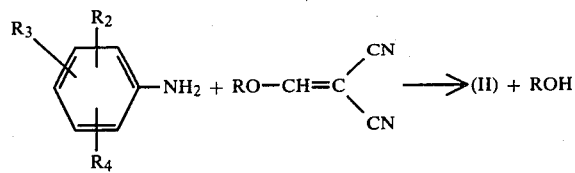

wherein R represents alkyl.

This process, which is suitable for preparing both the known and the new starting materials, is known from the U.S. patent specifications referred to above.

In addition, German Offenlegungsschrift Nos. 2,535,769 and 2,601,052 disclose anilinomethylenemalononitrile compounds for combating insects which damage plants.

Throughout this specification, the term "helminths" is to be understood as meaning parasitic nematoda, cestoda and trematoda in the gastrointestinal tract or in other organs.

Among the endoparasites which occur in warm-blooded animals, the helminths especially cause great harm. Animals attacked by these parasites are not only retarded in their growth and exhibit a marked diminution in their useful performance, but are to some extent so severely harmed that they die. In order to prevent, or at least to reduce, losses in animal husbandry, which can be quite substantial if an outbreak of helminthiasis assumes epidemic proportions in livestock, unremitting efforts are being made to provide agents for combating helminths, including their development stages.

Accordingly, a large number of substances having anthelmintic action are known, but they are unable to satisfy the requirements made of them in the desired manner, because for example they do not have a sufficient potency when administered in well tolerated doses or they cause undesirable side-effects, such as toxamia, when administered in therapeutic doses.

The anilinomethylenemalonnitrile derivatives of the formula I are distinguished by good anthelmintic action against nematoda, cestoda and, especially, trematoda. In particular, their action against fasciolida (*Fasciola hepatica*) is to be highlighted.

The following compounds are especially preferred on account of their action against fascioliasis:
N-(2,2-dicyanovinyl)-N-(2,4-dichlorobenzyl)-3,5-bis-trifluoromethyl-aniline.
N-(2,2-dicyanovinyl)-N-(3,4-dichlorobenzyl)-3,5-bis-trifluoromethyl-aniline.
N-(2,2-dicyanovinyl)-N-(2,6-dichlorobenzyl)-3,5-bis-trifluoromethyl-aniline.
N-(2,2-dicyanovinyl)-N-(2,3-dibromopropyl)-3,5-bis-trifluoromethyl-aniline.
N-(2,2-dicyanovinyl)-N-(4-fluorobenzyl)-3,5-bis-trifluoromethyl-aniline.

EXAMPLE 1

Preparation of
N-(2,2-dicyanovinyl)-N-(3,4-dichlorobenzyl)-3,5-bis-trifluoromethyl-aniline With stirring, 16.8 g of potassium tert-butylate are added by small amounts to a solution of 45.7 g of 3,5-bis-trifluoromethyl-N-(2,2-dicyanovinyl)-aniline in 200 ml of dimethyl sulphoxide. The solution is kept for 4 hours at 40° C. With further stirring, 20.8 ml of 3,4-dichlorobenzyl chloride in 20 ml of dimethyl sulphoxide are added dropwise and the reaction mixture is then stirred for 12 hours at 40° C. The mixture is then poured onto 2 liters of ice and the precipitated product is extracted with chloroform. The chloroform solution is washed with water, dried over sodium sulphate and the chloroform is distilled off. The crude product is chromatographed over a silica gel column with methyl acetate/hexane (1:3 v/v) as eluant, yielding 15 g of the desired product in the form of yellow crystals with a melting point of 102°–103° C.

Analysis: $C_{19}H_9Cl_2F_6N_3$

| % | C | H | N | Cl |
|---|---|---|---|----|
| calculated: | 49.16 | 1.95 | 9.05 | 15.28 |
| found: | 49.3 | 2.1 | 9.4 | 15.3 |

The following compounds were prepared by methods and analogous to that described in this Example:

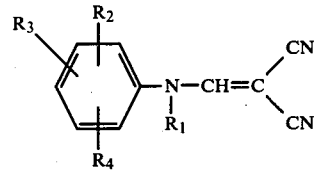

| No. | $R_1$ | $R_2$ | $R_3$ | $R_4$ | Physical data |
|---|---|---|---|---|---|
| 1 | —CH$_2$—CH$_3$=CH$_2$ | 3-CF$_3$ | 4-Cl | H | liquid |
| 2 | —CH$_2$—C≡CH | H | H | H | mp. 96°–98° C. |
| 3 | —CH$_2$—C≡CH | H | 4-Cl | H | mp. 87°–90° C. |
| 4 | —CH$_2$—C≡CH | 2-Cl | H | H | mp. 84°–88° C. |
| 5 | —CH$_2$—C≡CH | 2-Cl | 4-CH$_3$ | H | mp. 81°–82° C. |
| 6 | —CH$_2$—C≡CH | 3-Cl | H | 5-Cl | mp. 124°–127° C. |
| 7 | —CH$_2$—C≡CH | 2-Cl | 4-Cl | 5-Cl | mp. 125°–128° C. |
| 8 | —CH$_2$—C≡CH | 2-Br | 4-Br | H | mp. 124°–126° C. |
| 9 | —CH$_2$—CHBr—CH$_2$Br | 3-CF$_3$ | 5-CF$_3$ | H | mp. 93°–96° C. |
| 10 | —CH$_2$—CH=CH—CH$_3$ | 3-CF$_3$ | 4-Cl | H | liquid |
| 11 | —CH$_2$—C≡CH | 3-Cl | H | H | liquid |
| 12 | —CH$_2$—C≡CH | 2-Cl | H | 5-Cl | mp. 105°–108° C. |
| 13 | —CH$_2$—CH=CH$_2$ | 3-CF$_3$ | 4-Cl | H | liquid |
| 14 | —CH$_2$—C≡CH | 3-Cl | 4-Cl | H | mp. 74° C. |
| 15 | benzyl | H | H | H | mp. 97°–99° C. |
| 16 | benzyl | H | 4-Cl | H | mp. 168°–171° C. |
| 17 | benzyl | 3-Cl | H | H | liquid |
| 18 | benzyl | 2-Cl | H | H | mp. 100°–102° C. |
| 19 | benzyl | 3-Cl | 4-Cl | H | mp. 64°–66° C. |
| 20 | benzyl | 3-Cl | H | 5-Cl | mp. 112°–114° C. |
| 21 | benzyl | 2-Cl | H | 5-Cl | mp. 88°–90° C. |
| 22 | benzyl | 2-Cl | 4-Cl | 5-Cl | mp. 137°–140° C. |
| 23 | benzyl | 2-CH$_3$ | 4-Cl | H | mp. 126°–128° C. |
| 24 | benzyl | 3-NO$_2$ | H | H | liquid |
| 25 | 4-fluorobenzyl | 3-CF$_3$ | 5-CF$_3$ | H | mp. 107°–109° C. |
| 26 | 4-chlorobenzyl | 3-CF$_3$ | 5-CF$_3$ | H | mp. 117°–119° C. |
| 27 | 4-chlorobenzyl | 3-CF$_3$ | 5-CF$_3$ | H | liquid |

-continued

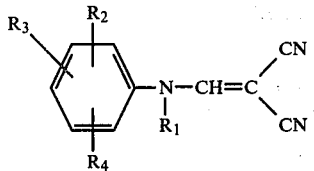

| No. | R₁ | R₂ | R₃ | R₄ | Physical data |
|---|---|---|---|---|---|
| 28 | 2-chlorobenzyl | 3-CF₃ | 5-CF₃ | H | mp. 90° C. |
| 29 | 2,4-dichlorobenzyl | 3-CF₃ | 5-CF₃ | H | liquid |
| 30 | 3,4-dichlorobenzyl | 3-CF₃ | 5-CF₃ | H | mp. 102°–103° C. |
| 31 | 2,6-dichlorobenzyl | 3-CF₃ | 5-CF₃ | H | mp. 169°–171° C. |
| 32 | 2,6-dichlorobenzyl | H | 4-Nitro | H | mp. 172° C. |
| 33 | 2,6-dichlorobenzyl | 2-CN | H | H | mp. 85° C. |
| 34 | 3,4-dichlorobenzyl | 2-CN | H | H | mp. 98° C. |
| 35 | 3-methylbenzyl | 3-CF₃ | 5-CF₃ | H | mp. 75°–77° C. |
| 36 | 2-methylbenzyl | 3-CF₃ | 5-CF₃ | H | mp. 109°–110° C. |
| 37 | 4-cyanobenzyl | 3-CF₃ | 5-CF₃ | H | mp. 115°–118° C. |
| 38 | 2,4-Dichlorobenzyl | 3-NO₂ | 5-NO₂ | H | |
| 39 | benzyl | 5-NO₂ | 5-NO₂ | | |
| 40 | —CH₂—C≡CH | 3-NO₂ | 5-NO₂ | H | |
| 41 | —CH₂—CH=CH | 2-CH₃ | 4-NO₂ | 5-Cl | mp. 107°–108° C. |

The following tests demonstrate the anthelmintic action of the anilinomethylenemalononitrile derivatives of the formula I.

1. Tests on mice attacked by *Nematospiroides dubius*

The active substances are administered in the form of a suspension with a stomach probe to white mice infected with *Nematospiroides dubius*. Five animals are used per test. The active compounds are administered to each animal once daily on 3 successive days. The animals are then sacrificed on the 8th day after the start of the treatement and dissected.

Evaluation is made after dissection of the animals by counting the number of nematoda in the intestine. Untreated mice which were infected at the same time and in the same way were used as control.

The compositions are tolerated by the mice without any symptoms.

2. Tests on mice attacked by *Nippostrongylus brasiliensis*

The active substances are administered in the form of a suspension with a stomach probe to white mice infected with *Nippostrongylus brasiliensis*. Five animals are used for each test. The active compounds are administered once daily to each group of animals on successive days. The daily dose per animal is 100 mg of active compound/kg of body weight. The animals are then sacrificed on the 4th day after the start of the treatment and dissected. Evaluation is made after dissection of the test animals by comparing the number of parasites remaining in the intestine with an untreated control which had been infected in the same way at the same time.

3. Tests on mice attacked by *Hymenolepis nana*

The active substances are administered in the form of a suspension with a stomach probe to white mice which have been artificially infected with *Hymenolepis nana*. Five animals are used for each test. The active compounds are administered to each group of animals once daily on 3 successive days. The animals are sacrificed on the 4th day after the start of the treatment and dissected. Evaluation is made after dissection of the animals by comparing the number of tape worms present in the intestine with an untreated control group which was infected at the same time in the same way.

4. Tests on rats infected with liver fluke (*Fasciola hepatica*)

White laboratory rats are infected with liver flukes (*Fasciola hepatica*). After expiry of the prepatent period, three infected rats per test are each treated once daily on 3 successive days with an active substance of the formula I in the form of a suspension using a stomach probe. Two weeks after administration of the active compound, the experimental animals are sacrificed and examined for the presence of liver flukes.

The results are reported in the following table:

| Active substance | Dose in mg/kg | number of liver flukes | % age reduction compared with control |
|---|---|---|---|
| A | 3 × 30 | 0/0/0 | 100 |
| B | 3 × 10 | 0/0/0 | 100 |
| C | 3 × 30 | 0/0/0 | 100 |
| D | 3 × 30 | 0/0/0 | 100 |
| E | 3 × 30 | 0/0/0 | 100 |
| F | 3 × 30 | 0/0/0 | 100 |
| G | 3 × 300 | 0/0/0 | 100 |
| H | 3 × 300 | 0/0/0 | 100 |

Active substances (compounds)

A: N-(2,2-dicyanovinyl)-N-(2,3-dibromopropyl)-3,5-bis-trifluoromethylaniline

B: N-(2,2-dicyanovinyl)-N-propargyl-2,4,5-trichloroaniline

C: N-(2,2-dicyanovinyl)-N-benzyl-2,4,5-trichloroaniline

D: N-(2,2-dicyanovinyl)-N-(2,4-dichlorobenzyl)-3,5-bis-trifluoromethylaniline

E: N-(2,2-dicyanovinyl)-N-(3-chlorobenzyl)-3,5-bis-trifluoromethylaniline

F: N-(2,2-dicyanovinyl)-N-(2-chlorobenzyl)-3,5-bis-trifluoromethylaniline

G: N-(2,2-dicyanovinyl)-N-(3,4-dichlorobenzyl)-3,5-bis-trifluoromethylaniline

H: N-(2,2-dicyanovinyl)-N-(2,6-dichlorobenzyl)-3,5-bis-trifluoromethylaniline

The compositions of the present invention are used for combating helminths in domestic animals and productive livestock, such as cattle, sheep, goats, horses, pigs, cats, dogs and poultry. They can be administered to the animals in both individual and repeated doses. Depending on the species of animal, the individual doses are preferably administered in amounts between 0.5 and 100 mg/kg of body weight. A better action is often attained by protracted administration, or it is possible to manage with lower total doses. The active compounds, or mixtures containing them, can also be added to feeds and to troughs. The ready-prepared feeds contain the active compounds of the formula I preferably in a concentration of 0.005 to 0.1% by weight. The compositions can be administered to the animals perorally or in the form of solutions, emulsions, suspensions (drenches), powders, tablets, boluses and capsules. Conventional solid carriers are used for preparing these formulations, for example kaolin, talc, bentonite, common salt, calcium phosphate, cotton seed flour or liquids which do not react with the active compounds, such as oils and other solvents and diluents which are harmless to the animal organism. Provided the physical and toxicological properties of salutions or emulsions permit it, the active compounds can also be administered to the animals by subcutaneous injection.

If the anthelmintic compositions are in the form of feed concentrates, then suitable carriers are for example hay, production feeds, cereal feeds or protein concentrates. In addition to the active compounds, such feeds can contain additives, vitamins, antibiotics, chemotherapeutical agents or other pesticides, chiefly bacteriostats, fungistats, coccidiostats or also hormone preparations, substances having anabolic action or other substances which promote growth, enhance the quality of the flesh of slaughter animals, or are otherwise beneficial to the organism. They can also be combined with other anthelmintic agents, whereby their activity spectrum is broadened and adapted to given circumstances.

Examples of such substances are:

Namatocides

For example Absonal, Alcopar, Anthelcide, Ascaridol, Banminth II, Bephenium, Bradosol, Cambendazol, Chlorophos, Chlorthion, Coumaphos, Cyanin, Destomycin, Diethylcarbamazine, Dichlorphen, DDVP, 1,4-di-(D-glyconyl)piperazine, Dithiazonin, Dow ET/70, Dowco 132, Dymanthine HCl, Egressin, Gainex, Hexachlorophene, hexylresorcinol, Ionit, Levamisol, Mepacrine, methylene violet, ethyl 1-methyl-tridecylpiperazinium-4-carboxylate, Methyridine, Monopar, Narlene, Neguvon, Nematodin, Nemural, Nidanthel, Parbendazol, Parvex Phenothiazine, piperazine, polymethylenepiperazine, Promethazine, Pyrantel, Pyranthiazine, pyrvinium embonate, Rametin, Ronnel, Santonin Shell 1808, Stilbazium, Tetramisol, Thenium, Thiabendazole, Thymolan, Vermella, Nebendazol;

Cestodicides

For example Acranil, Arecoline, Atebrin, Bithionol, dithionol oxide, Bunamidin, Cestodin, Cambendazol, dibutyl tin dilaurate, Dichlorophen, dioctyl tin dichloride, dioctyl tin dilaurate, Filixic acid, Hexachlorophen, Nidanthel, Terenol, Yomesan.

The anthelmintic compositions of the present invention are prepared in a manner known per se by homogeneously mixing and/or grinding active compounds of the formula I with suitable carriers, with or without the addition of dispersants or solvents which are inert to the active compounds.

The active substances may be processed to the following formulations:

Solid formulations

Granules (coated granules, impregnated granules and homogeneous granules); water-dispersible active substance concentrates (wettable powders).

Liquid formulations

Solutions, pastes, emulsions (especially ready for use emulsions).

For dusts and wettable powders, the granular size of the carriers is advantageously up to about 0.1 mm and for granules 10.500$\mu$ (0.01–0.5 mm).

In the solid formulations, the active substance concentrations are from 0.5 to 80%, and in the liquid formulations from 0.5 to 15%.

These mixtures can also contain additives which stabilise the active substance and/or nonionic, anionic and cationic substances which ensure for example an improved wettability (wetting agents) and dispersibility (dispersants).

Water-dispersible powder mixture

Composition:

25 parts of active substance of the formula I 3 parts of a mixture of polyoxyethylene-tall oil ester-urea 7 parts of polyvinyl pyrrolidone 31.5 parts of highly disperse silicic acid 33.5 parts of bolus alba.

The active substance is homogeneously mixed together with the polyoxyethylene tall oil ester-urea mixture and the polyvinyl pyrrolidone with the addition of about 30% of the silicic acid in a planetary mixer. The remainder of the silicic acid and the bolus alba are then added and the mixture is mixed in suitable mixers until homogeneous, and then ground to a particle size of less than 20$\mu$ in a disc mill.

What is claimed is:

1. A process for the control of parasitic helminths in warm blooded animals which comprises administering orally or subcutaneously to the animal an anthelmintically effective amount of a compound of the formula

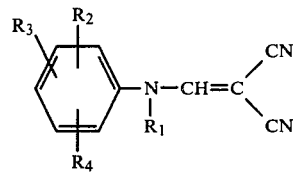

wherein $R_1$ represents halogenalkyl containing 1 to 6 carbon atoms in the alkyl moiety, $C_3$–$C_4$ alkenyl, $C_3$–$C_5$ alkenyl $C_3$–$C_5$ alkynyl or a benzyl radical which is unsubstituted or substituted by 1 to 2 halogen atoms, 1 to 2 $C_1$–$C_2$ alkyl radicals, or by a cyano or a trifluoromethyl group, $R_2$ represents hydrogen, $C_1$–$C_4$ alkyl, halogen, the trifluoromethyl group, the nitro group or the cyano group, $R_3$ represents hydrogen, halogen, the trifluoromethyl group or the nitro group, and $R_4$ represents hydrogen or halogen, with the proviso that, if $R_1$ represents the $C_3$ alkynyl radical or the unsubstituted benzyl group, $R_2$ and $R_3$ may not be trifluoromethyl.

2. The process of claim 1, wherein in said compound $R_2$ and $R_3$, each independently of the other, represent hydrogen, halogen, methyl, trifluoromethyl or nitro.

3. The process of claim 1, wherein in said compound $R_2$ and $R_3$, each independently of the other, represent chlorine, methyl, trifluoromethyl or nitro, and $R_4$ represents hydrogen or chlorine.

4. The process of claim 1 for the control of parasitic trematod.

5. The process of claim 1 for the control of parasitic Fasciola Lepatica.

* * * * *